(12) United States Patent
Lord et al.

(10) Patent No.: US 10,561,608 B2
(45) Date of Patent: *Feb. 18, 2020

(54) DRY POWDER VANCOMYCIN COMPOSITIONS AND ASSOCIATED METHODS

(71) Applicant: SAVARA INC., Austin, TX (US)

(72) Inventors: John Lord, Austin, TX (US); Jaakko Taneli Jouhikainen, Austin, TX (US); Herman E. Snyder, West Lafayette, IN (US); Pravin Soni, Sunnyvale, CA (US); Mei-Chang Kuo, Palo Alto, CA (US)

(73) Assignee: Savara Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/536,457

(22) Filed: Aug. 9, 2019

(65) Prior Publication Data

US 2019/0380955 A1 Dec. 19, 2019

Related U.S. Application Data

(63) Continuation of application No. 14/965,172, filed on Dec. 10, 2015, now Pat. No. 10,420,722, which is a continuation of application No. 14/083,983, filed on Nov. 19, 2013, now Pat. No. 9,572,774, which is a continuation-in-part of application No. PCT/US2012/038775, filed on May 21, 2012.

(60) Provisional application No. 61/487,971, filed on May 19, 2011.

(51) Int. Cl.
| | | |
|---|---|---|
| *A61K 9/00* | (2006.01) | |
| *A61K 9/16* | (2006.01) | |
| *A61K 38/14* | (2006.01) | |
| *A61K 9/48* | (2006.01) | |

(52) U.S. Cl.
CPC .......... *A61K 9/0075* (2013.01); *A61K 9/1617* (2013.01); *A61K 9/1623* (2013.01); *A61K 9/4816* (2013.01); *A61K 9/4866* (2013.01); *A61K 38/14* (2013.01); *Y10T 428/2982* (2015.01)

(58) Field of Classification Search
None
See application file for complete search history.

(56) References Cited

U.S. PATENT DOCUMENTS

| | | |
|---|---|---|
| 3,067,099 A | 12/1962 | Mccormick et al. |
| 5,582,825 A | 12/1996 | Sakaguchi et al. |
| 5,847,004 A | 12/1998 | Lai |
| 5,922,761 A | 7/1999 | Lai |
| 5,997,912 A | 12/1999 | Schlesinger et al. |
| 6,123,936 A | 9/2000 | Platz et al. |
| 6,231,851 B1 | 5/2001 | Platz et al. |
| 6,316,502 B1 | 11/2001 | Lai et al. |
| 6,372,258 B1 | 4/2002 | Platz et al. |
| 6,475,523 B1 | 11/2002 | Staniforth et al. |
| 6,582,728 B1 | 6/2003 | Platz et al. |
| 6,586,008 B1 | 7/2003 | Batycky et al. |
| 7,252,840 B1 | 8/2007 | Batycky et al. |
| 7,322,352 B2 | 1/2008 | Minshull et al. |
| 7,345,051 B2 | 3/2008 | Zhou et al. |
| 7,355,074 B2 | 4/2008 | Davis et al. |
| 7,612,045 B2 | 11/2009 | Eldridge |
| 2002/0187105 A1 | 12/2002 | Zou et al. |
| 2003/0113272 A1 | 6/2003 | Staniforth |
| 2004/0247628 A1 | 12/2004 | Lintz et al. |
| 2005/0147567 A1 | 7/2005 | Kuo |
| 2005/0152849 A1 | 7/2005 | Staniforth |
| 2005/0249675 A1 | 11/2005 | Hung et al. |
| 2006/0054166 A1 | 3/2006 | Knoch et al. |
| 2006/0142208 A1 | 6/2006 | Boucher et al. |
| 2006/0147389 A1 | 7/2006 | Staniforth et al. |
| 2006/0211697 A1 | 9/2006 | Huang et al. |
| 2006/0276473 A1 | 12/2006 | Bostion et al. |
| 2007/0014739 A1 | 1/2007 | Eldridge et al. |
| 2007/0196461 A1 | 8/2007 | Weers |
| 2007/0218013 A1 | 9/2007 | Baker et al. |
| 2008/0020003 A1 | 1/2008 | Hill et al. |
| 2008/0026056 A1 | 1/2008 | Guimberteau et al. |
| 2008/0031824 A1 | 2/2008 | Smyth et al. |
| 2008/0057129 A1 | 3/2008 | Lerner et al. |
| 2008/0063606 A1 | 3/2008 | Tarara et al. |
| 2008/0160092 A1 | 7/2008 | Batycky et al. |
| 2008/0214481 A1 | 9/2008 | Challoner et al. |
| 2009/0025713 A1 | 1/2009 | Keller et al. |
| 2009/0181101 A1 | 7/2009 | Rademacher et al. |
| 2009/0269396 A1 | 10/2009 | Cipolla et al. |
| 2010/0029551 A1 | 2/2010 | Raff et al. |
| 2010/0063005 A1 | 3/2010 | Fiala |
| 2010/0087416 A1 | 4/2010 | Griffith et al. |

(Continued)

FOREIGN PATENT DOCUMENTS

| | | |
|---|---|---|
| WO | 1997041833 | 11/1997 |
| WO | 2001013893 | 3/2001 |
| WO | 2001032144 | 10/2001 |
| WO | 2003037303 | 5/2003 |
| WO | 2009020481 | 2/2009 |
| WO | 2009042187 | 4/2009 |
| WO | 2009052411 | 4/2009 |
| WO | 2009055571 | 4/2009 |
| WO | WO2009050217 A2 | 4/2009 |
| WO | 2010003465 | 1/2010 |

(Continued)

OTHER PUBLICATIONS

Wennerstrum, Powder and Bulk Engineering, Feb. 2000, p. 1-8.
Pharma Test, Tapped or Bulk Density or Apparent Volume Test Instrument, p. 1-4, retrieved online on Sep. 24, 2014.
Vehring et al. "Pharmaceutical Particle Engineering via Spray Drying." Pharmaceuticaly Research [online], May 2008 [Retrieved on Aug. 1, 2012), vol. 25, Iss. 5, pp. 999-1022, Retrieved from the internet: <URL: http://www.ncbi.nlm.nih.gov/pmc/artides/PMC2292490/>, see entire document, especially Figs. 1-10.

(Continued)

*Primary Examiner* — Jennifer A Berrios
(74) *Attorney, Agent, or Firm* — Matthew S. Gibson; Ryan P. Cox; Reed Smith LLP

(57) ABSTRACT

Dry powder vancomycin compositions and methods for administering and preparing such compositions are provided.

20 Claims, 7 Drawing Sheets
(6 of 7 Drawing Sheet(s) Filed in Color)

(56) References Cited

U.S. PATENT DOCUMENTS

| | | |
|---|---|---|
| 2010/0092526 A1 | 4/2010 | Baker et al. |
| 2010/0158957 A1 | 6/2010 | Surber et al. |
| 2010/0196455 A1 | 8/2010 | Malinin |
| 2010/0258118 A1 | 10/2010 | Morton |
| 2010/0282247 A1 | 11/2010 | Kadrichu |
| 2010/0303917 A1 | 12/2010 | Watson et al. |
| 2010/0305062 A1 | 12/2010 | Onsoyen et al. |
| 2010/0330061 A1 | 12/2010 | Conner |
| 2011/0003001 A1 | 1/2011 | Baker |

FOREIGN PATENT DOCUMENTS

| | | |
|---|---|---|
| WO | 2010042549 | 4/2010 |
| WO | 2010042553 | 4/2010 |
| WO | WO2010111641 A2 | 9/2010 |
| WO | WO2010111680 A2 | 9/2010 |
| WO | 2010124141 | 10/2010 |

OTHER PUBLICATIONS

Nettey, et al. "Formulation and testing of vancomycin loaded albumin microspheres prepared by spray-drying." Journal of Microencapsulation [online], Sep. 2006 [Retrieved on Aug. 1, 2012], vol. 23, Issue 6, pp. 632-642, Retrieved from the Internet: URL:http://www.ncbinlm.nih.gov/pubmed/17118879>.

De Jesus, et al., "Pulmonary verses Systemic Delivery of Antibiotics: Comparison of Vancomycin Dispositions in the Isolated Rat Lung." Antimicrobial Agents and Chemotherapy, vol. 51, No. 10, Aug. 6, 2007, pp. 3771-3774.

"Leucine." Handbook of Pharmaceutical Excipients. Fifth Edition, 2006, pp. 412.

Gadgil, "A comparative study between high potency dry powder inhalation and nebulized solution of vancomycin hydrochloride for lung delivery." Aug. 11, 2011, pp. FP-109, Retrieved from the Internet: URL:http://search.proquest.com/pqdtscieng/docview/889930798as02134 [retrieved on Nov. 11, 2014].

DRY POWDER VANCOMYCIN COMPOSITIONS AND ASSOCIATED METHODS

CROSS-REFERENCE TO RELATED APPLICATIONS

This application is a continuation of U.S. patent application Ser. No. 14/965,172, filed Dec. 10, 2015, which is a continuation of U.S. patent application Ser. No. 14/083,983, filed Nov. 19, 2013, now U.S. Pat. No. 9,572,774, which is a continuation-in-part of International Application No. PCT/US12/38775 filed May 21, 2012, which was published as International Publication No. WO 2012/159103, and which claims the benefit of U.S. Patent App. Ser. No. 61/487,971 filed May 19, 2011, all of which are incorporated by reference herein in their entirety.

BACKGROUND

Vancomycin is a glycopeptide antibiotic used in the prophylaxis and treatment of infections caused by Gram-positive bacteria. Vancomycin is the international nonproprietary name (INN) corresponding to the compound with the following formula:

Vancomycin has been administered intravenously for systemic therapy, as well as orally in the treatment of pseudomembranous colitis. Vancomycin has also been used off-label in a nebulized aerosol form for the treatment of various infections of the upper and lower respiratory tract. However, the use of an approved drug in an off-label manner may put a patient at risk as the safety and efficacy have not been studied and/or the appropriate dose may not be given. Furthermore, delivery by nebulization can take up to 20 minutes, which is a significant burden to patients. Currently, there are no known commercially available dry powder inhalable forms of vancomycin.

SUMMARY

The present disclosure generally relates to dry powder compositions and methods for administering and preparing such compositions.

In one embodiment, the present disclosure provides a composition comprising vancomycin or a pharmaceutically acceptable salt thereof, wherein the composition is a dry powder.

In another embodiment, the present disclosure also provides a method comprising administering a dry powder composition comprising vancomycin or a pharmaceutically acceptable salt thereof to a subject via pulmonary administration.

In yet another embodiment, the present disclosure provides a method comprising spray drying an aqueous composition comprising vancomycin or a pharmaceutically acceptable salt thereof and a hydrophobic amino acid so as to form a dry powder composition.

The features and advantages of the present invention will be apparent to those skilled in the art. While numerous It has been proposed that vancomycin acts by inhibiting proper cell wall synthesis in Gram-positive bacteria. More specifically, it is believed that vancomycin prevents incorporation of N-acetylmuramic acid (NAM) and N-acetylglucosamine (NAG)glycan subunits into the peptidoglycan matrix; which forms the major structural component of Gram-positive cell walls. The binding of vancomycin to the terminal D-alanyl-D-alanine moieties of the NAM/NAG-peptides prevents their incorporation into the peptidoglycan matrix.

changes may be made by those skilled in the art, such changes are within the spirit of the invention.

DRAWINGS

The patent or application file contains at least one drawing executed in color. Copies of this patent or patent application publication with color drawing(s) will be provided by the Office upon request and payment of the necessary fee.

Some specific example embodiments of the disclosure may be understood by referring, in part, to the following description and the accompanying drawings.

FIG. 1 is a graph depicting the aerodynamic particle size distribution of a dry powder vancomycin composition (Lot SA010) as measured using the Andersen Cascade Impactor and Monodose RS01 Model 7 inhaler.

FIG. 2 is a graph depicting the effect of leucine content on the delivery efficiency of dry powder vancomycin compositions (Lots SA002, SA006, SA007, SA008 and SA009) as measured using the fast screening impactor and Monodose RS01 Model 7 inhaler. Emitted dose (%) is the amount of drug in the dry powder that exits the inhaler as a percentage of the initial amount of drug in the dry powder present in the capsule. Fine particle fraction (%) is the amount of drug in the dry powder having an aerodynamic size less than 5 µm as a percentage of the emitted dose. Delivery efficiency (%) is the amount of drug in the dry powder having an aerodynamic diameter less than 5 µm as a percentage of the initial amount of drug in the capsule.

Figure 11:
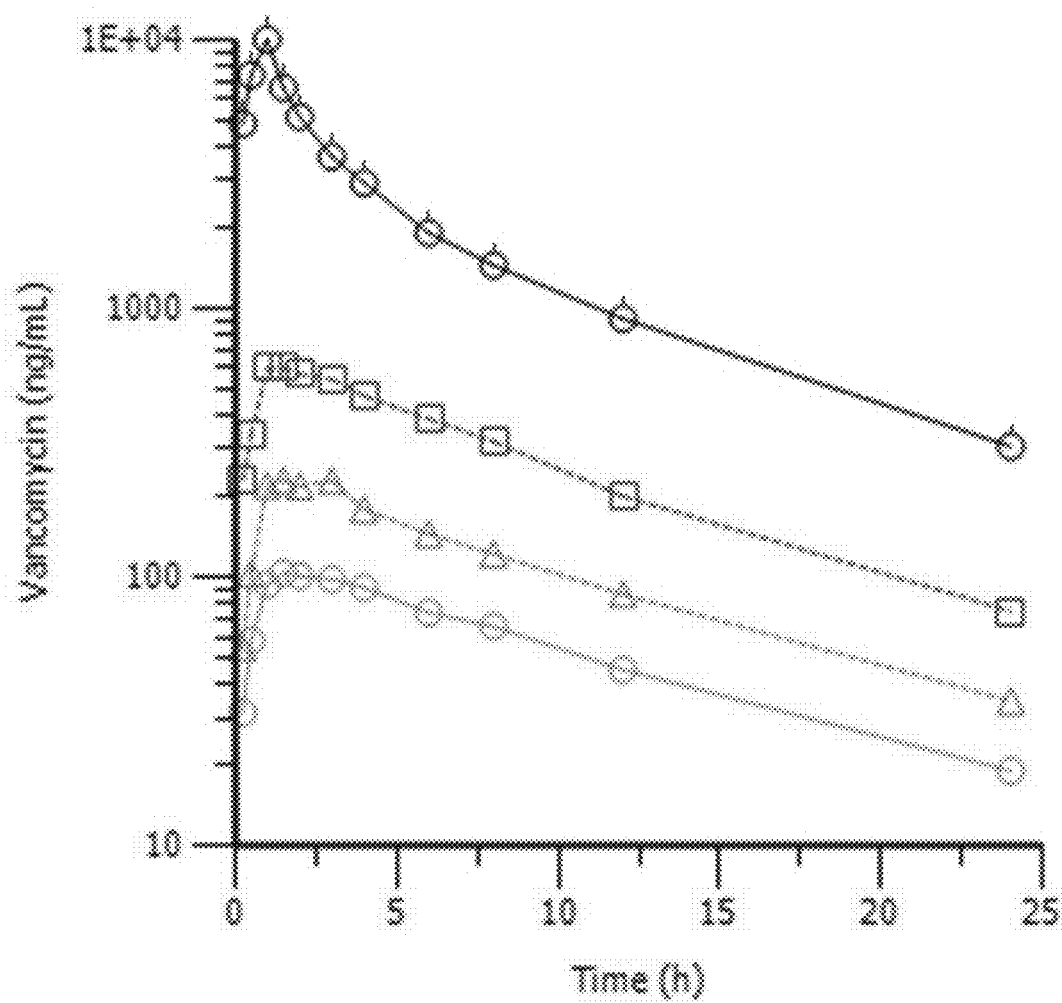

FIG. 11 is a graph depicting plasma concentrations as a function of time (semi-log) after a single dose administration of a vancomycin dry powder composition (Lot G-11-026-1) or intravenous administration of vancomycin (inhaled vancomycin dose 16 mg, circle; inhaled vancomycin dose 32 mg, triangle; inhaled vancomycin dose 80 mg, square; Intravenous infusion 250 mg over 60 min, circle with line).

Figure 12:

FIG. 12 is an image of slug of dry powder.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to dry powder vancomycin compositions and methods for administering and preparing such compositions. In some embodiments, a composition of the present disclosure may be administered to a subject via pulmonary administration in an amount effective to treat and/or prevent a bacterial infection in the subject. Administration of an effective amount of a composition of the present disclosure may be particularly useful in treating a gram-positive bacterial infection in a subject suffering from pneumonia, cystic fibrosis, bronchiectasis, or other chronic lung disease with a bacterial infection of the subject's airway and/or lung.

In one embodiment, a composition of the present disclosure is a dry powder comprising vancomycin or a pharmaceutically acceptable salt thereof. As used herein, the term vancomycin includes analogues and derivatives of vancomycin. As used herein, the term "dry" means that the composition has a moisture content such that the particles are readily dispersible in an inhalation device to form an aerosol. In some embodiments, this moisture content may be below about 10% by weight water, below about 7% by weight water, below about 5% by weight water or below about 3% by weight water. Furthermore, as used herein, the term "powder" means a composition that consists of finely dispersed solid particles that are capable of being readily dispersed in an inhalation device and subsequently inhaled by a subject so that the particles reach the lungs to permit penetration into the upper and lower airways. Thus, the powder is said to be "respirable." In some embodiments, a dry powder composition of the present disclosure may have a tap density greater than about 0.4 g/cm$^3$, greater than about 0.45 g/cm$^3$ or greater than about 0.5 g/cm$^3$. While vancomycin may be predominately used in the descriptions contained in this disclosure, it should be understood that the present disclosure may be practiced with any other glycopeptide antibiotics (e.g. vancomycin, teicoplanin, telavancin, bleomycin, ramoplanin, and decaplanin), and derivatives and analogues thereof, among other things, to treat certain gram positive infections.

In certain specific embodiments, a dry powder composition of the present disclosure comprises vancomycin, or a pharmaceutically acceptable salt thereof, present in an amount of about 90% by weight of the composition, the powder having a tap density of greater than about 0.4 g/cm$^3$, and further comprises leucine in an amount of about 10% by weight of the composition.

In some embodiments, a dry powder composition of the present disclosure may comprise particles having an average particle size of less than or equal to about 10 microns (μm) in diameter as defined by the mass median aerodynamic diameter (MMAD) (measured using cascade impaction). In some embodiments, at least 95% of the particles have a MMAD of less than about 10 μm. In some embodiments, the diameter may be less than or equal to about 7 μm. In other embodiments, the diameter may be less than or equal to about 5 μm. In certain specific embodiments, the diameter may be between about 0.5 μm and about 5 μm in diameter, particularly about 1 μm to about 3 μm. Dry powder compositions of the present disclosure comprising particles having an average particle size of less than or equal to about 10 μm in diameter may be particularly useful for delivery via an oral inhalation device.

In other embodiments, a dry powder composition of the present disclosure may comprise particles having an average particle size of greater than or equal to about 10 μm in diameter as defined by MMAD (measured using cascade impaction). In some embodiments, at least 95% of the particles have a MMAD of greater than about 10 μm. In certain specific embodiments, the particle size may be between about 10 μm and about 50 μm in diameter, particularly about 20 μm to about 40 μm. Dry powder compositions of the present disclosure comprising particles having an average particle size of greater than or equal to about 10 μm in diameter may be particularly useful for nasal delivery.

In some embodiments, the particles may be hollow. In some embodiments, the particles may be porous. In some embodiments, the particles may have a spheroidal shape distribution, which may be relatively uniform. In some embodiments, the vancomycin potency as measured by microbial activity is effectively unchanged when compared to the unformulated drug (i.e. within 5% of the drug).

Vancomycin or a pharmaceutically acceptable salt thereof suitable for use in the present disclosure is generally available through various commercial vendors. Examples of suitable pharmaceutically acceptable salts of vancomycin include, but are not limited to, vancomycin hydrochloride, vancomycin sulfate, etc.

In some embodiments, in addition to vancomycin or a pharmaceutically acceptable salt thereof, a composition of the present disclosure may further comprise one or more additives. One example of a suitable additive includes a hydrophobic amino acid. Such hydrophobic amino acids may include, but are not limited to, tryptophan, tyrosine, leucine, trileucine and phenylalanine. In some embodiments, it may be desirable to include a hydrophobic amino acid in a composition of the present disclosure so as to improve the physical stability and/or dispersibility of the composition, improve the chemical stability of vancomycin or a pharmaceutically acceptable salt thereof, and/or to alter the taste of the composition by masking the bitter taste of vancomycin and its salts, and/or to alter the rate the composition is absorbed into the systemic circulation from the lung (e.g., increase or slow the rate). While not wishing to be bound to any particular theory, it is currently believed that the hydrophobic amino acid additive remains on the surface of the particles and protects them from moisture and light, thereby increasing the stability of the formulation.

Another example of a suitable additive includes a carbohydrate bulking agent. Such carbohydrate bulking agents may include, but are not limited to, lactose, mannitol, trehalose, raffinose, and maltodextrins. In some embodiments, it may be desirable to include a carbohydrate bulking agent in a composition of the present disclosure so as to improve the physical stability of the composition. Furthermore, in some embodiments, the carbohydrate bulking agent may also improve the chemical stability of vancomycin or a pharmaceutically acceptable salt thereof. Other additives known to those of ordinary skill in the art may also be included.

Generally, additives suitable for use in the compositions of the present disclosure may be included in an amount of about 50% or less by weight of the composition, 30% or less by weight of the composition, or 10% or less by weight of the composition. In other embodiments, additives suitable for use in the compositions of the present disclosure may be included in an amount of from about 10% to about 30% by weight of the composition. In other embodiments, additives suitable for use in the compositions of the present disclosure may be included in an amount of from about 10% to about 20% by weight of the composition.

The compositions of the present disclosure may further comprise pharmaceutically acceptable auxiliary substances or adjuvants, including, without limitation, pH adjusting and buffering agents and/or tonicity adjusting agents, such as, for example, sodium acetate, sodium lactate, sodium chloride, potassium chloride, calcium chloride, etc. Leucine has the dual benefit of also modifying the pH. Similarly, the compositions of the present disclosure may contain pharmaceutically acceptable carriers and excipients including microspheres, microcapsules, nanoparticles or the like.

In certain embodiments, the dry powder composition may be reconstituted and the resulting reconstituted powder may have a pH greater than 3.0, preferably greater than 3.5 and most preferably greater than 4.0.

As previously mentioned, administration of an effective amount of a dry powder vancomycin composition may be particularly useful in alleviating symptoms and/or treating subjects suffering from conditions including, but not limited to pneumonia and cystic fibrosis with gram-positive bacterial infections, and/or colonization of the airways and/or lung parenchyma by bacteria or other pathogens susceptible to vancomycin or its derivatives. Other conditions may include, but are not limited to, bronchitis, bronchiectasis, diffuse panbronchiolitis, bronchiolitis, bronchiolitis obliterans, bronchiolitis obliterans organizing pneumonia (BOOP), pneumonia of any cause, including but not limited to community acquired pneumonia, nosocomial pneumonia and ventilator associated pneumonia (VAP). Examples of gram-positive bacterial infections may include, but are not limited to, bacterial infections by *Streptococcus pneumoniae*, and *Staphylococcus aureus*, including methicillin-resistant *Staphylococcus aureus*.

As will be recognized by one of ordinary skill in the art, the effective amount needed to treat a particular condition or disease state will depend on the pathogen, individual, the condition, length of treatment, the regularity of treatment, the type of vancomycin used, and other factors, but can be readily determined by one of ordinary skill. The patient can achieve a desired dosage by inhaling an appropriate amount of the composition.

A dry powder composition of the present disclosure may be delivered to a subject by any means so long as the solid particles of the dry powder composition are capable of being inhaled by a subject so that the particles reach the lungs to permit penetration into the upper and lower airways. In certain embodiments, a dry powder composition of the present disclosure may be delivered to a subject by placing the dry powder within a suitable dosage receptacle in a sufficient amount. Suitable dosage receptacles include those used in reservoir devices (e.g., devices that contain more than one dose in which the device itself meters the dose) or factory-metered dose devices (e.g., devices in which each dose is contained in either a single unit or multiple units). In one example, a suitable reservoir device may have a dosage receptacle that fits within a suitable inhalation device to allow for the aerosolization of the dry powder composition by dispersion into a gas stream to form an aerosol and then delivering the aerosol so produced from a mouthpiece attached for subsequent inhalation by a subject in need of treatment. Such a dosage receptacle includes any container enclosing the composition known in the art such as gelatin, hydroxypropyl methyl cellulose or plastic capsules with a removable portion or body that can be cut or pierced that allows dispersal of the dry powder composition (e.g., via a gas stream directed into the container and via centrifugal force). Such containers are exemplified by those shown in U.S. Pat. No. 4,227,522 issued Oct. 14, 1980; U.S. Pat. No. 4,192,309 issued Mar. 11, 1980; and U.S. Pat. No. 4,105,027 issued Aug. 8, 1978. Suitable containers also include those used in conjunction with GlaxoSmithKline's Ventolin Rotahaler brand powder inhaler or Fisons' Spinhaler brand powder inhaler. Another suitable unit-dose container which provides a superior moisture barrier is formed from an aluminum foil plastic laminate. The powder composition is filled by weight or by volume into the depression in the formable foil and hermetically sealed with a covering foil-plastic laminate. Such a container for use with a powder inhalation device is described in U.S. Pat. No. 4,778,054 and is used with GlaxoSmithKline's Diskhaler (U.S. Pat. Nos. 4,627,432; 4,811,731; and 5,035,237). All of these references are incorporated herein by reference. In other embodiments, a dry powder composition of the present disclosure may be delivered to a subject via a tracheal tube.

In some embodiments, compositions of the present disclosure may be prepared by spray drying an aqueous mixture of vancomycin or a salt thereof and a pharmaceutically acceptable carrier under conditions sufficient to provide a respirable dry powder composition. In some embodiments, the dry powder composition is substantially amorphous.

Generally speaking, spray drying is a process in which a homogeneous aqueous mixture of vancomycin or a salt thereof and the carrier is introduced via a nozzle (e.g., a two fluid nozzle), spinning disc or an equivalent device into a hot gas stream to atomize the solution thereby forming fine droplets which subsequently mix into a hot gas stream. The aqueous mixture may be a solution, suspension, slurry, or the like, but should be homogeneous to ensure uniform distribution of the components in the mixture and ultimately the powdered composition. Preferably the aqueous mixture is a solution. In some embodiments, the aqueous mixture may have a solids content of at least 1% by weight water. In other embodiments, the aqueous mixture may have a solids content of at least 2% by weight water. In other embodiments, the aqueous mixture may have a solids content of at least 4% by weight water. The solvent, generally water, rapidly evaporates from the droplets producing a fine dry powder having particles 1 to 5 µm in diameter.

In some embodiments, the spray drying is done under conditions that result in a substantially amorphous powder of homogeneous constitution having a particle size that is respirable, a low moisture content and characteristics that allow for ready aerosolization. In some embodiments, the particle size of the resulting powder is such that more than about 95% of the mass is in particles having a diameter of about 10 µm or less.

For the spraying process, such spraying methods as rotary atomization, pressure atomization and two-fluid atomization can be used. Examples of suitable devices are disclosed in U.S. Pat. No. 6,372,258, the contents of which are hereby incorporated by reference.

Alternatively, dry powder compositions may be prepared by other processes such as lyophilization and jet milling as disclosed in WO 91/16038, the disclosure of which is hereby incorporated by reference.

A number of formulation and processing strategies may be useful to improve, among other things, the storage and stability properties of the dry powder vancomycin compositions of the present disclosure. In certain embodiments, the vancomycin used may be chosen to be of a higher purity. In other embodiments, steps may be taken to avoid oxidation of vancomycin. For example, processing and packaging of the composition may be performed under nitrogen. Similarly, in some embodiments the processing and packaging may be performed to minimize exposure to direct light. Such steps may reduce light-mediated degradation of vancomycin. In some embodiments, steps may be taken to reduce the amount of moisture in the composition. Such steps may be useful to avoid hydrolysis, deamidation, and oxidation of vancomycin. As mentioned above, a carbohydrate bulking agent may be added to the composition, which also may improve chemical stability.

Furthermore, while the dry powder vancomycin compositions of the present disclosure have many advantageous properties, in certain embodiments, one particularly advantageous property is that the compositions may have a pharmacokinetic profile that is favorable for antibacterial efficacy of a time dependent bactericidal antibiotic, such as vancomycin, in that it may provide a prolonged high concentration of vancomycin in the lung, and thereby increase the time during which the minimum inhibitory concentrations of target pathogens are exceeded.

For example, in certain embodiments, upon administration of a dry powder vancomycin composition to a subject, the median amount of time necessary for the blood plasma levels of a subject to reach their maximum concentration of vancomycin ($T_{max}$) may be greater than or equal to about 30 minutes, greater than or equal to about one hour, or less than or equal to about six hours. In some embodiments, $T_{max}$ may be between about one hour and three hours. Similarly, in certain embodiments, the median amount of time necessary for blood plasma levels of a subject to decrease to one half of the total maximum concentration of vancomycin ($t_{1/2}$) may be greater than six hours. In some embodiments, $t_{1/2}$ may be about eight hours.

In certain embodiments, upon administration of a dry powder vancomycin composition to a subject, the mean maximum blood plasma concentration of vancomycin ($C_{max}$) may be within the range of about 50% to about 150% of about n×620 ng/mL, wherein n represents a factor to be multiplied and may be a value from 0.01 to 10 and when n=1 the dose is 80 mg.

In one particular embodiment, wherein the vancomycin or the pharmaceutically acceptable salt thereof is present in an amount of about 80 mg, the dry powder composition may provide a mean maximum blood plasma concentration of vancomycin within the range of about 50% to about 150% of about 620 ng/mL, a mean $AUC_{0-24\ h}$ value within the range of about 50% to about 150% of about 6,250 nghr/mL, and a median $T_{max}$ value within the range of about 0.75 hours to 3 hours, as measured following a single pulmonary administration. As would be recognized by one of skill in the art, for dry powder compositions containing lower or higher concentrations of vancomycin than 80 mg, the above ranges may be adjusted directly proportionally by the dose. Accordingly, in certain embodiments the present disclosure also provides compositions wherein the vancomycin or the pharmaceutically acceptable salt thereof is present in the dry powder composition in an amount of about n×80 mg and wherein the dry powder composition provides: a mean maximum blood plasma concentration of vancomycin ($C_{max}$) within the range of about 50% to about 150% of about n×620 ng/mL; an mean $AUC_{0-24\ h}$ value within the range of about 50% to about 150% of about n×6,250 nghr/mL; and a median $T_{max}$ value in the range of about 0.5 hours to about 6 hours, wherein the maximum blood plasma concentration of vancomycin, the $AUC_{0-24\ h}$ value, and the $T_{max}$ value are measured following a single pulmonary administration of the dry powder composition; wherein n represents a factor to be multiplied and may be a value from 0.01 to 10.

In some embodiments, the dry powder vancomycin compositions of the present disclosure may provide a delivery efficiency of 40% or more. In other embodiments, the dry powder vancomycin compositions of the present disclosure may provide a delivery efficiency of 60% or more. Delivery efficiency (%) is the amount of the dry powder having an aerodynamic diameter less than 5 µm as a percentage of the initial amount of dry powder in the capsule. Delivery efficiency is the emitted dose (%) (i.e., the amount of the dry powder that exits the inhaler as a percentage of the initial amount of the dry powder present in the capsule) multiplied by the fine particle fraction (%) (i.e., respirable amount or the amount of the dry powder having a mass median aerodynamic diameter (MMAD) of 5 µm or less as a percentage of the emitted dose).

In some embodiments, the dry powder vancomycin compositions of the present disclosure may provide an absolute bioavailability of 40% or more. Absolute bioavailability is calculated as $AUC_{0-inf}$ of vancomycin after the vancomycin composition administration divided by $AUC_{0-inf}$ of vancomycin after intravenous administration and adjusted for dose.

To facilitate a better understanding of the present invention, the following examples of certain aspects of some embodiments are given. In no way should the following examples be read to limit, or define, the entire scope of the invention.

Example 1

Dry powder vancomycin compositions were produced on a Buchi lab scale spray dryer at high yield (75-95%) and at two different batch sizes (1 g and 20 g) with no loss in purity. These powders exhibited very high delivery efficiencies and consistency across lots.

Figures 1, 2:
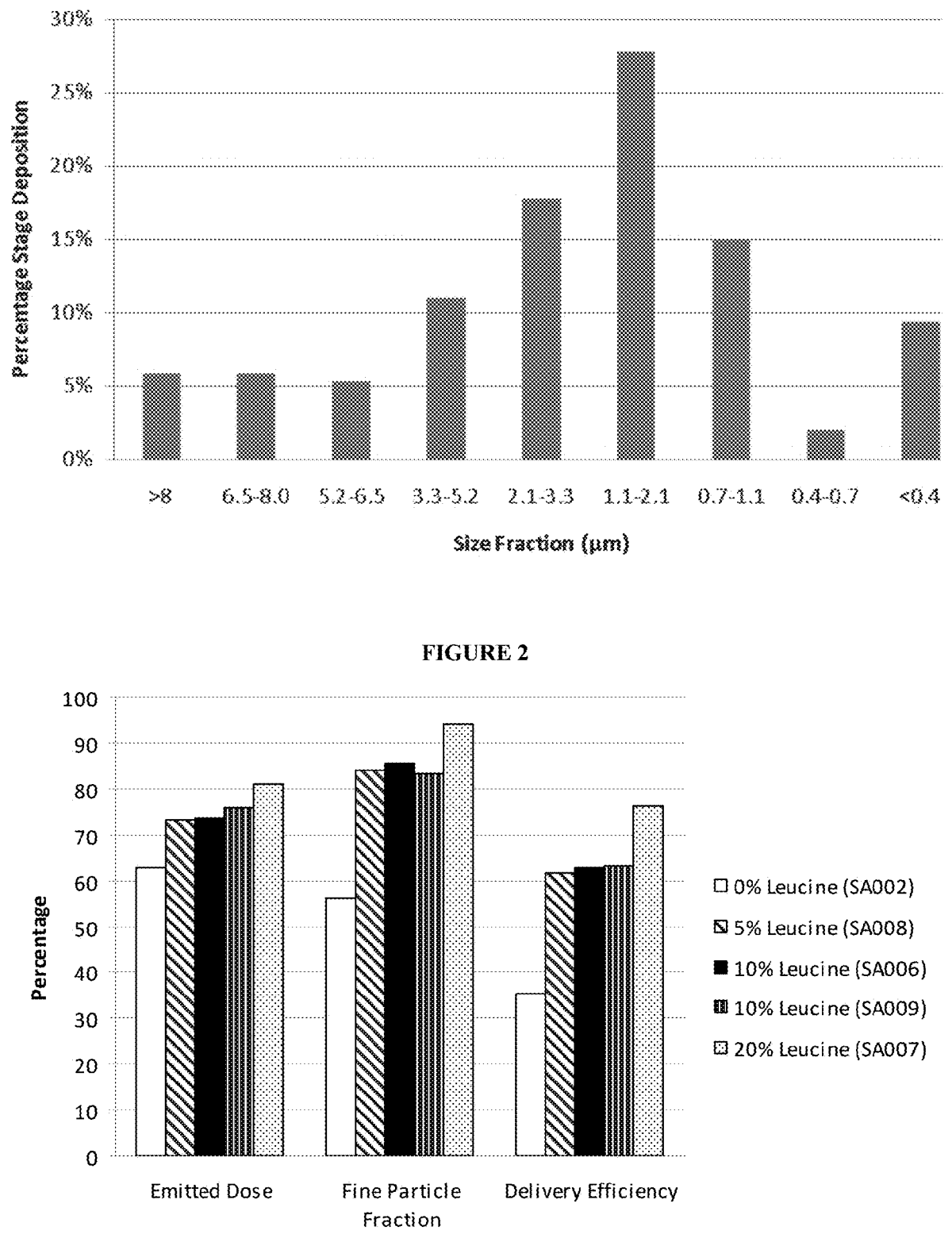

The full aerodynamic particle size distribution for the 20 g batch is depicted in FIG. 1 showing that the vast majority of the particle size distribution is less than 5 µm and that a significant proportion (approx. 59%) is within the ultra-fine particle fraction (3 µm) predictive of deep lung delivery.

Initial studies have shown that the emitted dose content uniformity of vancomycin powders easily meet the FDA's draft guidance specifications for aerosol dose content uniformity. This has been one of the greatest challenges facing the pulmonary drug delivery industry in the last 10 years. The specifications state that no more than 1 out of 10 actuations should be outside±20% of the label claim with no actuation outside±25% of the label claim.

In some embodiments, the delivery efficiency of dry powder vancomycin compositions may be improved through the addition of small amounts of leucine (FIG. 2).

The addition of leucine to vancomycin powders significantly reduces the water content of the powder and the mass median aerodynamic diameter. In addition, the addition of leucine results in powders with more physiologically acceptable pH values. See Table 1 below for the effect of leucine concentration on powder water content, particle size and reconstituted pH.

TABLE 1

| Attribute | API | 5% Leucine (Lot SA008) | 10% Leucine (Lot SA006) | 20% Leucine (Lot SA007) |
| --- | --- | --- | --- | --- |
| Water content by Karl Fischer (%) | n/a | 7.9 | 6.4 | 5.8 |
| MMAD by AeroSizer (µm) | n/a | 1.82 | 1.71 | 1.57 |
| Reconstituted pH | 3.0 | 4.0 | 4.2 | 4.4 |

Protocol for Making One Example of a Dry Powder Vancomycin Composition

Solution Preparation

An example batch formula is included in Table 2. The target mass of leucine is weighed into a beaker. The required mass of de-ionized water is added and mixed using a magnetic stir bar. Vancomycin hydrochloride is then added and the solution is stirred for 1.0-1.5 hours until visibly clear. The feedstock solution is prepared immediately before being spray dried. The solution concentration is approximately 4% w/w total dissolved solids.

TABLE 2

Batch formula for a nominal 90% vancomycin HCl, 10% leucine formulation (Lot SA010)

| Ingredient | Mass (g) |
| --- | --- |
| Vancomycin hydrochloride | 17.1 |
| Leucine | 1.9 |
| Water | 475.2 |

Processing Procedure

A benchtop spray drying system (Buchi model 191) with high efficiency cyclone is used to generate and collect the powder. For 19 g batch sizes, the powder is more conveniently recovered from the process stream across 4 cyclone powder collection events. The equilibrium drying condition is established using de-ionized water. When stable operation is obtained, the nozzle input is switched to feedstock solution. The solution is fed to the dryer until a quarter of the solution has been utilized and then the nozzle is switched back to water for approximately 5 minutes to clear the system. The dryer is then shutdown momentarily to allow for collector change-out, restarted immediately and lined-out on water prior to resuming feed solution.

The filled collector is rapidly capped on removal to minimize exposure to room humidity. Each collector is then transferred into individual glass sample vials within a low humidity dry glove box and the complete set of vials packaged into an aluminum pouch with desiccant and heat-sealed.

Figure 3:
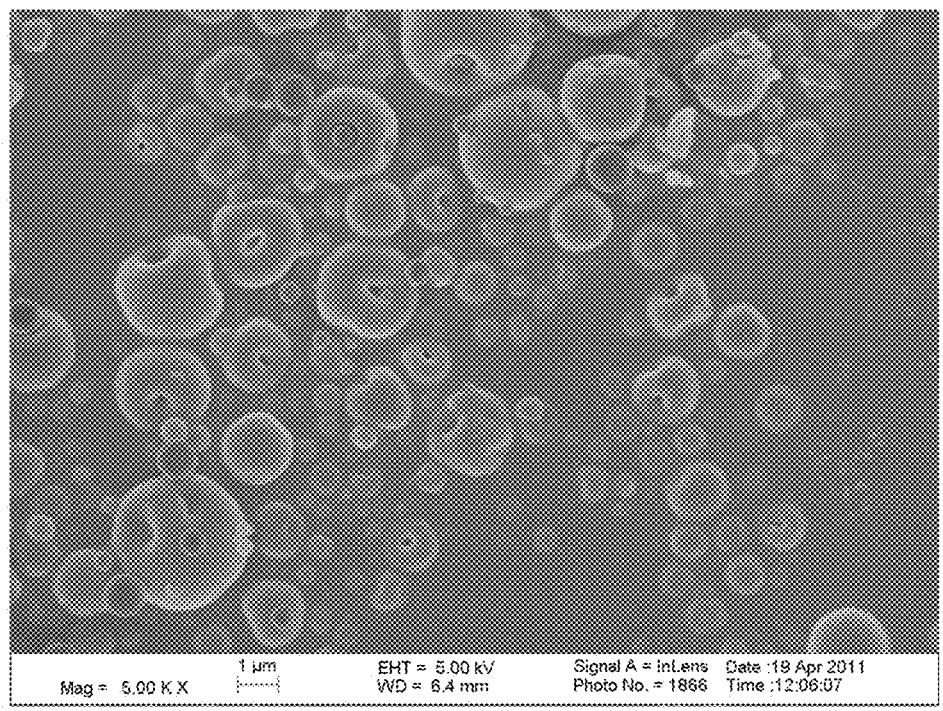
FIG. 3 is an image of lab-scale dry powder vancomycin particles (Lot SA010) obtained using a scanning electron microscope.

FIG. 3 depicts a scanning electron microscope (SEM) image of a vancomycin-leucine powder formulation from Lot SA010.

Stability of Dry Powder Vancomycin Compositions

Figure 4:
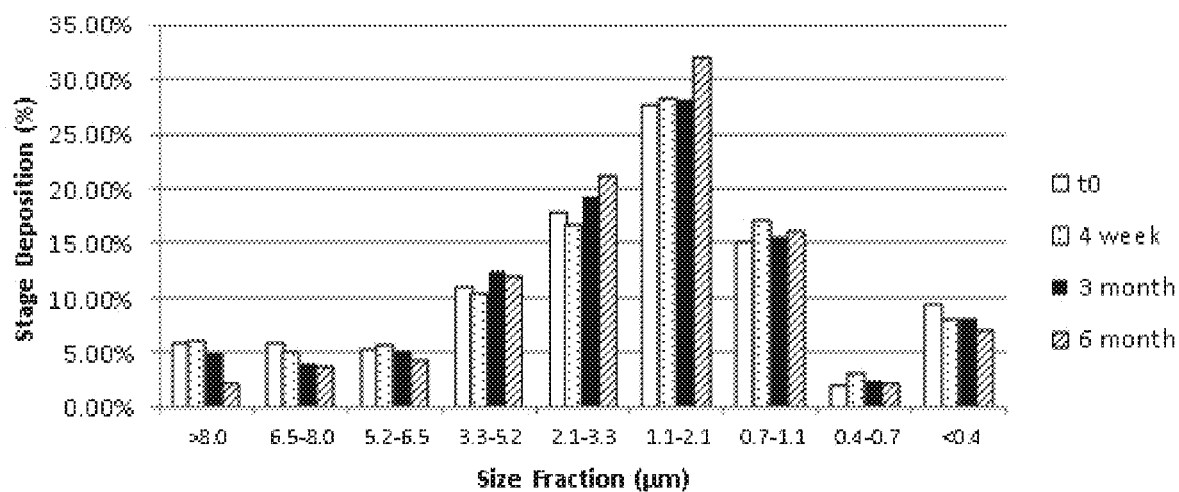
FIG. 4 is a graph depicting the aerodynamic particle size distribution of a dry powder vancomycin composition (Lot SA010) stored at 25° C. and 60% relative humidity (RH) for a period up to 6 months as measured using the Andersen Cascade Impactor and Monodose RS01 Model 7 inhaler.
Figure 5:
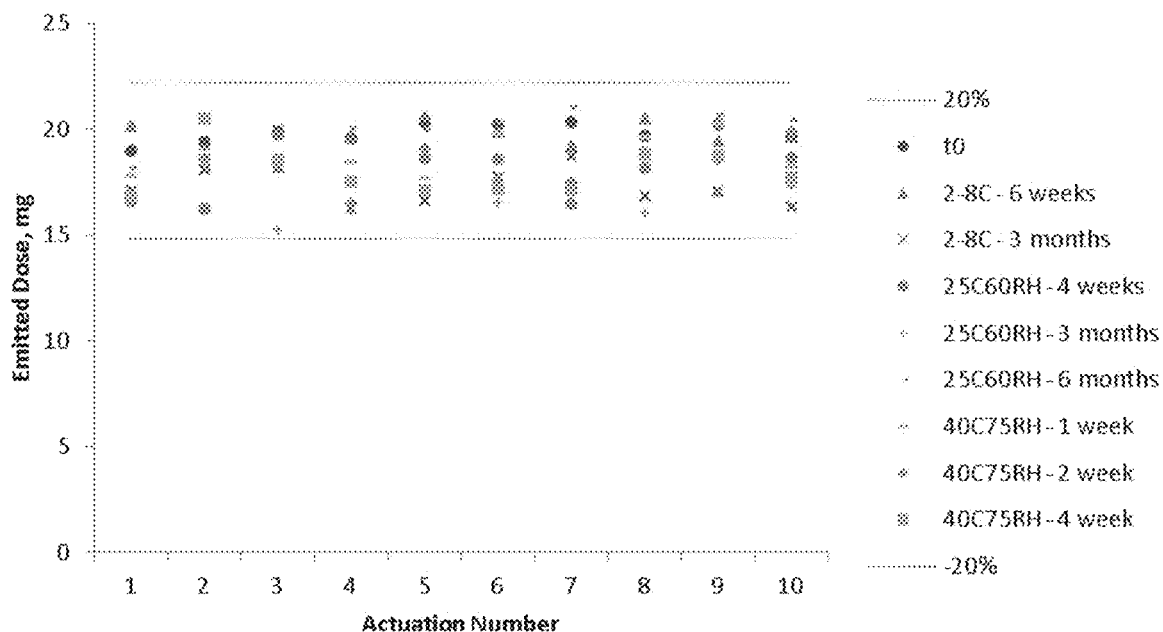
FIG. 5 is a graph depicting the emitted dose content uniformity under 3 different stability conditions for a period up to 6 months of 10 consecutive actuations through a Monodose RS01 Model 7 inhaler compared to FDA draft guidance specification limits of ±20% (Lot SA010).

Results from a 6-month stability study conducted on Lot SA010 show that the aerosol particle size distribution does not change with time (FIG. 4). Similarly, the emitted dose does not change and remains within FDA draft guidance limits of ±20% of the mean (FIG. 5). The chemical stability from this initial study predicted a composition that would require refrigerated storage.

Example 2

As previously mentioned, in some embodiments, dry powder vancomycin compositions of the present disclosure may be prepared using spray drying methods. Such methods have proven to be very efficient and exhibit excellent batch to batch consistency.

Table 3 below shows yield, primary particle size and water content data for batch sizes ranging from 25 g to 100 g, which were prepared using spray drying methods. $X_{10}$, $X_{50}$ and $X_{90}$ are the mass diameter of particles to which 10%, 50% and 90% of the distribution is smaller, respectively. ND=Not determined.

Figure 6:
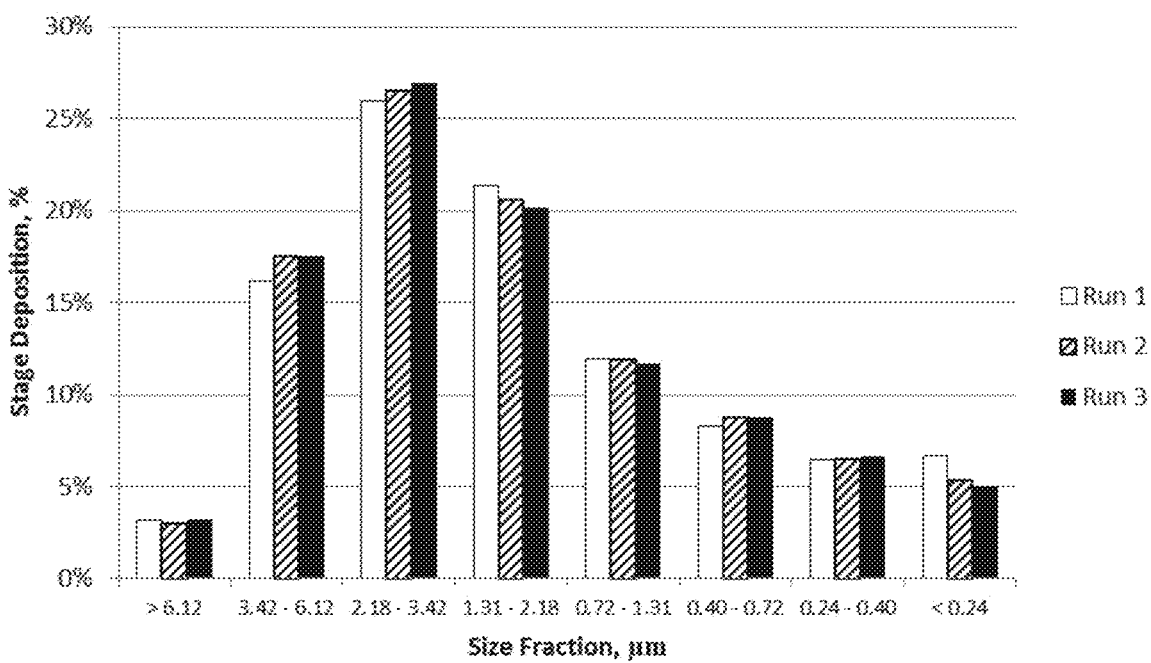
FIG. 6 is a graph depicting the aerodynamic particle size distribution of a dry powder vancomycin composition of the present disclosure (Lot G-11-26-1) as measured from three Monodose RS01 Model 7 inhalers tested at 100 L/min for 2.4 s (equivalent to 4 L) using a Next Generation Impactor.

Additionally, the full aerodynamic particle size distribution for Lot G-11-26-1 is included in FIG. 6 and shows that the vast majority of the particle size distribution is less than 5 μm (85%) and that a significant proportion (approx. 70%) is within the ultra-fine particle fraction (<3 μm) predictive of deep lung delivery.

TABLE 3

| Lot # | Lot Size (g) | Yield (%) | $X_{10}$ (μm) | $X_{50}$ (μm) | $X_{90}$ (μm) | Water Content (%) |
|---|---|---|---|---|---|---|
| G-11-18 | 25 | 86 | 0.51 | 1.20 | 2.55 | 5.77 |
| G-11-19 | 25 | 89 | 0.54 | 1.25 | 2.49 | 5.10 |
| D-11-039 | 50 | 86 | 0.47 | 1.33 | 2.53 | 3.99 |
| D-11-040 | 100 | 92 | 0.46 | 1.34 | 2.47 | 3.78 |
| D-11-041 | 50 | ND | 0.47 | 1.31 | 2.46 | 4.10 |
| D-11-042 | 50 | 90 | 0.48 | 1.31 | 2.47 | 3.97 |
| D-11-043 | 100 | ND | 0.49 | 1.32 | 2.50 | 3.72 |
| D-11-044 | 75 | 92 | 0.52 | 1.42 | 3.61 | 3.90 |
| D-11-045 | 75 | 91 | 0.49 | 1.33 | 2.87 | 4.34 |
| D-12-001 | 50 | 87 | 0.44 | 1.24 | 2.59 | 4.39 |
| D-12-002 | 50 | 84 | 0.42 | 1.25 | 2.59 | 4.81 |
| D-12-003 | 50 | 87 | 0.44 | 1.26 | 2.55 | 4.35 |
| D-12-004 | 75 | 88 | 0.46 | 1.27 | 2.57 | 4.55 |
| D-12-006 | 25 | 91 | 0.45 | 1.28 | 2.63 | 4.70 |

Figure 7:
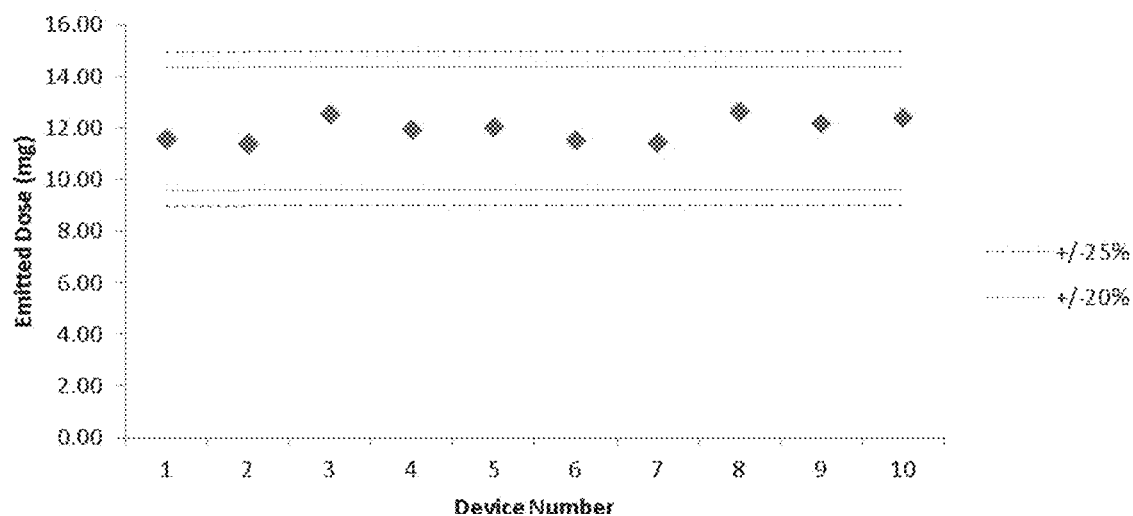
FIG. 7 is a graph depicting the emitted dose content uniformity across ten Monodose RS01 Model 7 inhalers tested at 100 L/min for 2.4 s (equivalent to 4 L) for lot G-11-26-1. The ±20% and ±25% represent the FDA draft guidance limits.

FIG. 7 shows that the emitted dose content uniformity for Lot G-11-26-1 meets the FDA's draft guidance specifications for aerosol dose content uniformity (i.e., no more than 1 out of 10 actuations should be outside±20% of the label claim with no actuation outside±25% of the label claim).

Stability

A summary of the 6-month stability study for Lot G-11-026-1 is included in Table 4.

TABLE 4

| | | Months | | | |
|---|---|---|---|---|---|
| Attribute | Specification | 0 | 1 | 3 | 6 |
| Appearance | White powder | Pass | Pass | Pass | Pass |
| Assay (mg) | 13.3-18.0 | 15.9 | 15.8 | 15.9 | 15.3 |
| Purity (%) | >85.0 | 95.6 | 95.5 | 95.8 | 95.5 |
| Emitted Dose (mg) | 9.1-13.6 | 12.0 | 11.9 | 12.2 | 11.9 |
| Fine Particle Dose (mg) | 6.3-11.7 | 8.9 | 8.9 | 9.2 | 9.1 |
| Water Content (%) | 3.0-8.0 | 4.5 | 4.6 | 4.1 | 4.1 |

Example 3

Figure 8:
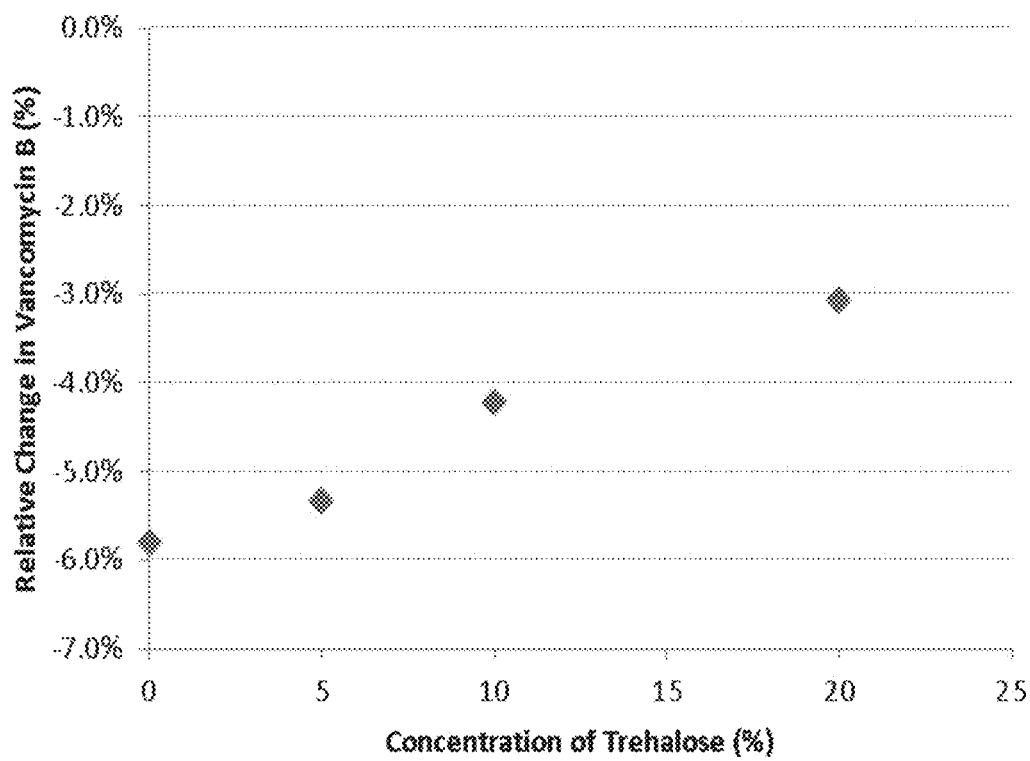
FIG. 8 is a graph depicting the effect of trehalose concentration on the chemical stability of a dry powder vancomycin composition of the present disclosure at 50° C. for 4 weeks.

A carbohydrate bulking agent was included in a vancomycin-leucine formulation. The chemical stability of this formulation was studied at 50° C. for 4 weeks. FIG. 8 shows that the addition of a carbohydrate bulking agent (e.g., trehalose) can improve the chemical stability of dry-powder vancomycin compositions of the present disclosure.

Figure 9:
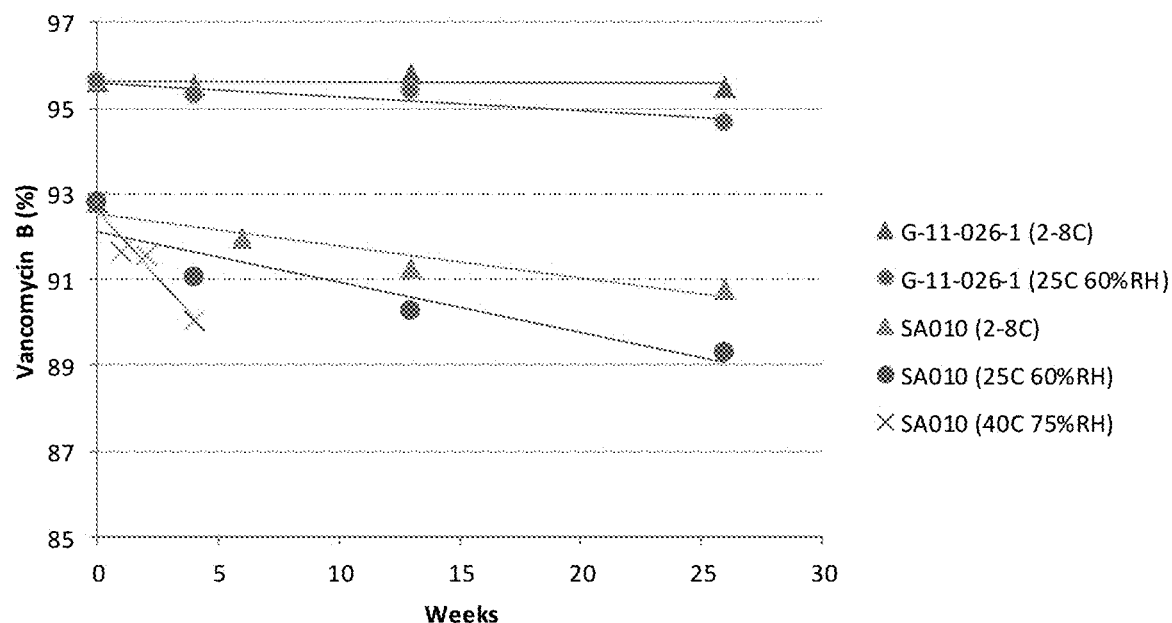
FIG. 9 is a graph depicting a comparison of two lots of dry powder vancomycin compositions containing 10% leucine. One contains no API or process modifications (Lot SA010) and the other has a more pure API source, was processed under nitrogen, precautions were taken to protect from light and the water content in the powder composition was lower (Lot G-11-026-1).

Two lots of a vancomycin composition containing 10% leucine were compared. One of the lots contained no process modifications (Lot SA010) and the other, was processed under nitrogen, protected from light, and protected from moisture (Lot G-11-026-1). As shown in FIG. 9, these modifications significantly retarded the degradation of vancomycin. Indeed, extrapolation of the data suggests the composition to be room temperature stable for at least 2 years.

Example 4

The powder production process has been successfully scaled-up from lab to pilot-scale equipment. The process can produce up to 1,000 g of powder per day at high yield (75%) and with no loss in purity.

Figure 10:
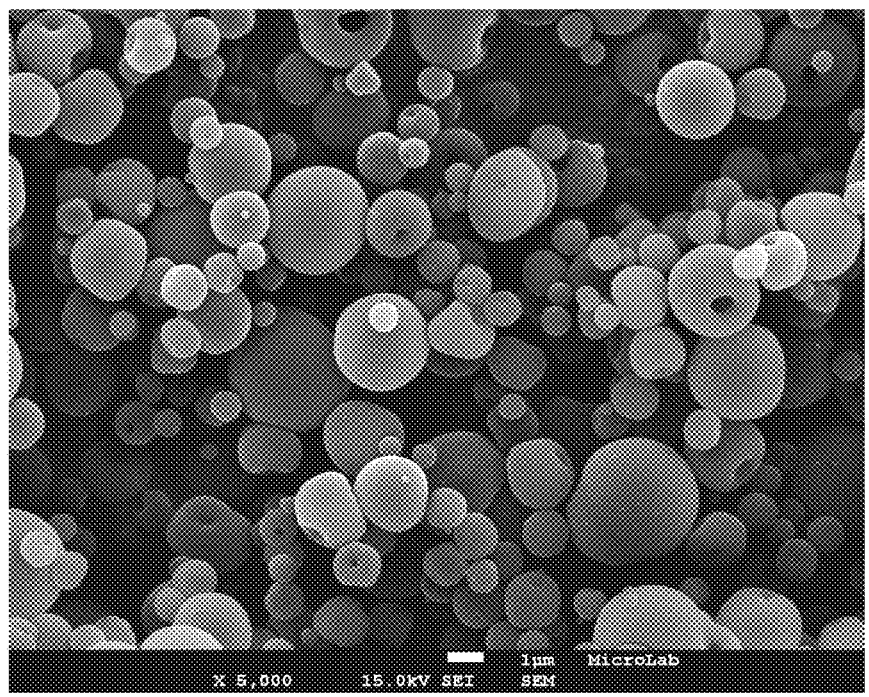
FIG. 10 is an image of pilot-scale dry powder vancomycin particles (Lot 19SA01.HQ00005) obtained using a scanning electron microscope.

FIG. 10 depicts a SEM image of particles from a 1,000 g lot (Lot 19SA01.HQ00005) manufactured on a Niro Mobile Minor "2000" spray dryer.

Table 5 below shows powder testing data from two scaled-up lots. Table 6 shows the corresponding final product test results for Lot 19SA01.HQ00002.

TABLE 5

| Lot # | Lot Size (g) | Yield (%) | $X_{10}$ (μm) | $X_{50}$ (μm) | $X_{90}$ (μm) | Water Content (%) |
|---|---|---|---|---|---|---|
| 19SA01.HQ00002 | 1 000 | 75 | 0.49 | 1.83 | 3.92 | 4.7 |
| 19SA01.HQ00005 | 1 000 | 75 | 0.90 | 1.81 | 3.52 | 5.4 |

TABLE 6

| Attribute | Specification | Results |
|---|---|---|
| Appearance | White powder | Pass |
| Assay (mg) | 13.3-18.0 | 16.5 |
| Purity (%) | >85.0 | 96.0 |
| Emitted Dose (mg) | 9.1-13.6 | 12.4 |
| Fine Particle Dose (mg) | 6.3-11.7 | 8.0 |
| Water Content (%) | 3.0-8.0 | 4.7 |

Example 5

Following a single administration of a dry powder vancomycin composition (Lot G-11-062-1) in eighteen healthy volunteers, a slow absorption phase followed by an elimination phase were observed. The main pharmacokinetic parameters after single dose administration of the inhaled vancomycin composition and intravenous vancomycin are shown in Table 7. The corresponding mean plasma concentration curves over 24 h are shown in FIG. 11. $AUC_{0-t}$ refers to the area under the plasma concentration-time curve to the last measurable time point (24 h) calculated by the linear trapezoidal rule. $AUC_{0-inf}$ refers to the area under the concentration-time curve to infinity. $C_{max}$ refers to the maximum blood plasma concentration of vancomycin, and $T_{max}$ refers to the amount of time necessary to reach maximum blood plasma levels of vancomycin, and fin, refers to the elimination half-life associated with the terminal slope ($K_{el}$) of the semilogarithmic drug concentration-time curve, calculated as $0.693/K_{el}$.

TABLE 7

| Dose | | $t_{1/2}$ (h) | $T_{max}$ (h) | $C_{max}$ (ng/ml) | $AUC_{(0-t)}$ (h*ng/ml) | $AUC_{(0-inf)}$ (h*ng/ml) |
|---|---|---|---|---|---|---|
| Inhaled vancomycin | | | | | | |
| 16 mg | Mean | 8.45 | 2.08 | 108.8 | 1,209.6 | 1,461.4 |
| | SD | 2.02 | 0.80 | 33.2 | 237.7 | 257.2 |
| 32 mg | Mean | 8.65 | 1.83 | 231.5 | 2,379.8 | 3,051.1 |
| | SD | 0.53 | 0.61 | 89.6 | 975.4 | 959.1 |
| 80 mg | Mean | 8.04 | 1.33 | 617.8 | 6,257.9 | 7,135.7 |
| | SD | 1.30 | 0.41 | 230.0 | 1506.9 | 1,457.9 |
| IV vancomycin | | | | | | |
| 250 mg | Mean | 7.23 | 0.92 | 10,028.3 | 41,027.8 | 44,356.3 |
| | SD | 1.13 | 0.20 | 1767.7 | 2,696.0 | 3,623.4 |

The median $T_{max}$ value was more than one hour with all doses, suggesting a slow absorption of vancomycin from the lungs. There was a slight trend towards a shorter $T_{max}$ with increasing doses (16 mg: 2 h (range 1-3 h); 32 mg: 1.5 h (range 1-3 h); 80 mg: 1.25 h (range 1-2 h). The observed $T_{max}$ values were considerably higher than expected based on previously published results with inhaled antibiotic powder (TOBI Podhaler prescribing information, $T_{max}$ of 1 h with all tested doses ranging from 28 mg to 112 mg). The $C_{max}$ of vancomycin was very closely dose proportional between 16 mg and 80 mg (R>0.95). Likewise, very good dose linearity was observed in the AUC values between the different inhaled vancomycin doses (R>0.95). The absolute bioavailability of vancomycin after the administration of the vancomycin composition, based on the results from those subjects within each cohort who received both the vancomycin composition and IV infusion, was on average 49%±8% (calculated as $AUC_{0-inf}$ of vancomycin after the vancomycin composition administration divided by $AUC_{0-inf}$ of vancomycin after intravenous administration and adjusted for dose).

The $t_{1/2}$ with the different vancomycin dose levels was very consistent, approximately 8 h, and longer than the $t_{1/2}$ observed following intravenous infusion. The apparent prolongation of $t_{1/2}$ further suggests prolonged pulmonary absorption that continued to feed vancomycin into the systemic circulation during the elimination phase of the concentration curve.

This pharmacokinetic profile is very favorable for antibacterial efficacy of a time dependent (and concentration-independent at concentrations exceeding approximately 1 µg/ml) bactericidal antibiotic, such as vancomycin, in that it provides a more prolonged high concentration of vancomycin in the lung, and thereby increases the time during which the minimum inhibitory concentrations of target pathogens are exceeded.

Example 6

Filling of powder into capsules is ubiquitous in the pharmaceutical industry. Volumetric filling technology relies on good powder flow properties and consistent powder density to ensure that each unit volume of powder contains the same mass of powder. This is facilitated by compression of the powder in the volumetric well to produce a slug (FIG. 12) that can then be expelled into the capsule. Typically, improved filling reproducibility is achieved at higher compression forces. This technique works very well for most oral medications. Unfortunately, this type of filling approach presents some unique challenges for dry powder inhalation products that use capsules as the storage vessel for the drug. For dry powder inhalation products, compression of the powder can produce a slug that does not facilitate subsequent dispersion into sub-micron sized particles. This has led companies pursuing these types of products to seek filling technology that is less likely to compress the powder. Drum filling technology, as manufactured by Harro Hofliger for example, was developed to address this need.

While new filling technologies have enabled dry powder inhalation products to be filled, it is at the cost of a loss in product efficiency. Typically, either the emitted dose or the fine particle dose is lowered. The present invention, according to certain embodiments, describes a formulation that is not impacted by the filling process and exhibits a product efficiency comparable to filling techniques that do not compress the powder. Table 8 shows data generated using two different filling techniques and equipment. The Xceledose filler (Capsugel) uses gravimetric technology and does not apply any force to compress the powder. In contrast, the Modu-C filler (Harro Hofliger) uses volumetric technology and utilizes a vacuum to exert force on the powder to form a slug. The data show that despite the Modu-C exerting a force of −700 mBar vacuum, there is no impact on the aerosol particle size distribution.

TABLE 8

Comparison of aerodynamic particle size data for two powders with either no applied vacuum (Lot HQ00008, vacuum level 0 mBar) or a high applied vacuum (Lot HQ00005, vacuum level −700 mBar) using a Next Generation Cascade Impactor (Copley Instruments).

| Attribute | Xcelodose filled | Modu-C filled |
|---|---|---|
| Powder Lot | HQ00008 | HQ00005 |
| Vacuum level | None | −700 mBar |
| Aerodynamic Particle Size | | |
| Capsule | 11% | 17% |
| Device | 7% | 6% |
| Induction Port | 7% | 7% |
| Stage 1 (>6.12 µm) | 4% | 4% |
| Stage 2 (3.42 µm-6.12 µm) | 15% | 14% |
| Stage 3 (2.18 µm-3.42 µm) | 11% | 11% |
| Stage 4 (1.31 µm-2.18 µm) | 8% | 7% |
| Stage 5 (0.72 µm-1.31 µm) | 5% | 5% |
| Stage 6 (0.40 µm-0.72 µm) | 4% | 4% |
| Stage 7 (0.24 µm-0.40 µm) | 3% | 3% |
| MOC (<0.24 µm) | 3% | 3% |
| Nozzles | 10% | 12% |
| Summary | | |
| Emitted Fraction | 69% | 69% |
| Fine Particle Fraction (as % emitted) | 71% | 72% |
| Fine Particle Fraction (as % filled) | 49% | 50% |
| MMAD, µm | 2.5 | 2.5 |
| GSD, µm | 2.3 | 2.3 |

Similarly, Table 9 shows that the tapped bulk density of the powder is only minimally affected by vacuum level in a Modu-C fitted with a drum filling head. Further, comparison to the results from an earlier tapped density experiment using the same formulation show similar densities. These data are surprising and show that vancomycin formulations, according to certain embodiments of the present disclosure, are not significantly impacted by the compression forces applied by the Modu-C filler utilizing a drum filling head. It is likely that the lack of compressibility is responsible for the consistency of aerosol performance over the range of vacuum pressures studied.

TABLE 9

The effect of vacuum level on powder density (lot HQ00005) as measured in the Modu-C filler compared to the tapped bulk density of powder (lot HQ00002) measured using tapped density apparatus.

| Powder Lot | Vac Level | Vac S.P. (mBar) | Density (g/mL) | Density Increase |
|---|---|---|---|---|
| HQ00002 | None | 0 | 0.53 | 0 |
| HQ00005 | Low | −300 | 0.53 | −0.9% |
| HQ00005 | Mid | −500 | 0.54 | 1.0% |
| HQ00005 | High | −700 | 0.55 | 3.5% |

In conclusion, vancomycin formulations according to certain embodiments of the present disclosure appear less susceptible to compression than other dry powder formulations. This should afford greater flexibility with respect to filler selection and process development.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A composition comprising vancomycin or a pharmaceutically acceptable salt thereof, and leucine, wherein vancomycin or the pharmaceutically acceptable salt thereof is present in an amount from about 75% to about 95% by weight of the composition, wherein the leucine is present in an amount of at least 5% by weight of the composition, and wherein the composition is a dry powder.

2. The composition of claim 1, wherein the pharmaceutically acceptable salt comprises vancomycin hydrochloride.

3. The composition of claim 1, further comprising water, wherein water is present in an amount of less than 10% by weight of the composition.

4. The composition of claim 1, wherein an amount of a mode of an aerosol particle size distribution of the composition does not change by more than about 5% after 6 months of storage at 25° C. and 60% relative humidity.

5. The composition of claim 1, wherein an average particle size of the composition does not change by more than 5% after 6 months of storage at 25° C. and 60% relative humidity.

6. The composition of claim 1, wherein the composition provides a median $T_{max}$ value between one and three hours.

7. The composition of claim 1, wherein the composition provides a mean maximum blood plasma concentration of vancomycin ($C_{max}$) within the range of about 50% to about 150% of about n×620 ng/mL, wherein n is a value from 0.01 to 10 and n is 1 when the dose of vancomycin is 80 mg.

8. The composition of claim 1, wherein the dry powder composition provides a delivery efficiency of 40% or more.

9. The composition of claim 1, wherein the dry powder composition provides an absolute bioavailability of 40% or more.

10. The composition of claim 1, wherein the vancomycin or the pharmaceutically acceptable salt thereof is present in the dry powder composition in an amount of n×80 mg, and wherein the dry powder composition provides:

a mean maximum blood plasma concentration of vancomycin ($C_{max}$) within the range of about 50% to about 150% of about n×620 ng/mL;

a mean $AUC_{0\text{-}24\ h}$ value within the range of about 50% to about 150% of about n×6,250 nghr/mL; and a median $T_{max}$ value within the range of about 0.5 to about 6 hours, wherein the maximum blood plasma concentration of vancomycin, the $AUC_{0\text{-}24\ h}$ value, and the $T_{max}$ value are the pharmacokinetic parameters following a single pulmonary administration of the dry powder composition;

wherein n is a value from 0.01 to 10.

11. The composition of claim 1, wherein a stage of an aerosol particle size distribution of the dry powder is not changed by more than 1% after application of 700 mBar of vacuum.

12. The composition of claim 11, wherein the stage comprises a particle size range between about 0.2 μm and about 6.1 μm.

13. A method comprising administering a dry powder composition comprising vancomycin or a pharmaceutically acceptable salt thereof, and leucine, wherein vancomycin or the pharmaceutically acceptable salt thereof is present in an amount from about 75% to about 95% by weight of the composition and wherein the leucine is present in an amount of at least 5% by weight of the composition, to a subject via pulmonary administration.

14. The method of claim 13, wherein the pharmaceutically acceptable salt comprises vancomycin hydrochloride.

15. The method of claim 13, wherein the subject has a condition selected from the group consisting of pneumonia, cystic fibrosis, bronchitis, bronchiectasis, diffuse panbronchiolitis, bronchiolitis, bronchiolitis obliterans, and bronchiolitis obliterans organizing pneumonia (BOOP).

16. The method of claim 13, wherein the composition provides a median $T_{max}$ value between one and three hours.

17. The method of claim 13, wherein the composition provides a mean maximum blood plasma concentration of vancomycin ($C_{max}$) within the range of about 50% to about 150% of about n×620 ng/mL, wherein n is a value from 0.01 to 10 and n is 1 when the dose of vancomycin is 80 mg.

18. The method of claim 13, wherein the composition provides a median $t_{1/2}$ value greater than 6 hours.

19. The method of claim 13, wherein the dry powder composition provides a delivery efficiency of 40% or more.

20. The method of claim 13, wherein the dry powder composition provides an absolute bioavailability of 40% or more.

\* \* \* \* \*